United States Patent [19]
Bousack et al.

[11] Patent Number: 5,720,140
[45] Date of Patent: Feb. 24, 1998

[54] REINFORCEMENT FOR BUILDING ELEMENTS UNDER TENSION AND INSTALLATIONS PROVIDED THEREWITH

[75] Inventors: Herbert Bousack, Aachen; Klaus Menzel, Tübingen; Gottfried Sawade, Stuttgart, all of Germany

[73] Assignees: Forschungszentrum Julich GmbH, Julich; Eorschungs- und Materialprufanstalt des Landes Baden-Wurttemberg, Stuttgart, both of Germany

[21] Appl. No.: 583,089
[22] PCT Filed: Jul. 7, 1994
[86] PCT No.: PCT/DE94/00788
   § 371 Date: Feb. 8, 1996
   § 102(e) Date: Feb. 8, 1996
[87] PCT Pub. No.: WO95/02099
   PCT Pub. Date: Jan. 19, 1995

[30] Foreign Application Priority Data

Jul. 9, 1993 [DE] Germany .................. 43 22 862.3

[51] Int. Cl.⁶ .................................................. E04C 5/08
[52] U.S. Cl. .................. 52/223.14; 52/223.6; 52/223.8; 52/745.19
[58] Field of Search .................. 52/223.1, 223.6, 52/223.14, 223.8, 745.19

[56] References Cited

FOREIGN PATENT DOCUMENTS

| | | |
|---|---|---|
| 376116 | 7/1990 | European Pat. Off. |
| 529181 | 9/1993 | European Pat. Off. |

*Primary Examiner*—Christopher Kent
*Attorney, Agent, or Firm*—Herbert Dubno

[57] ABSTRACT

A method of producing and verifying integrity of a structure in which an elongated ferromagnetic reinforcements are magnetized externally of the structure with a magnetic field strength sufficient to detect magnetization at the structure after the reinforcing is embedded in concrete or another building material. For the evaluation of the integrity of the structure a magnetic field sensor is displaced along a surface of it and the magnetic field from the previously magnetized reinforcement is recorded as a function of displacement of the sensor.

5 Claims, 3 Drawing Sheets

REINFORCEMENT FOR BUILDING ELEMENTS UNDER TENSION AND INSTALLATIONS PROVIDED THEREWITH

SPECIFICATION

CROSS REFERENCE TO RELATED APPLICATIONS

This application is a national phase of PCT/DE 94/00788 filed 7 Jul. 1994 and based, in turn, on German national application P 43 22 862.3 under the International Convention.

FIELD OF THE INVENTION

The present invention relates reinforcements for tension-loaded structural parts or installation parts which are characterized by being magnetized, especially magnetized to saturation (remanent magnetization).

Such reinforcements can be used optionally for tension-loaded installations like bridges, tunnels, concrete roofs, conveyor belts or the like of optional structural materials like plastics, concrete, etc. An especially significant use is, however, in reinforced concrete structures with steel reinforcements under tension to which the subsequent description is largely directed.

Such magnetized reinforcements enable a noninvasive monitoring of the integrity of structures and installations equipped with the reinforcements by nondestructive testing processes based upon magnetic-field measurements.

The magnetization of the tensioning steel or reinforcement steel, together with or without a sheathing tube, is effected prior to incorporation in the reinforced structure or installation part and can be carried out by the manufacturer of the reinforcing steel or at the structural site directly prior to the incorporation thereof.

The magnetization is effected in a manner known per se with the aid of correspondingly dimensioned and wound coils connected with a power supply for controllable current supply and corresponding holding and guide elements which enable a passage of the elements to be magnetized through the coil.

The useful life of prestressed reinforced concrete structures is determined largely by the integrity of the tensioned reinforcement. High-strength steels which are used for reinforcing, can break as a result of stress-crack corrosion without warning.

Failures recently have indicated that even in the case of properly applied pressed sheathing tubes and without detectable action of corrosive substances, ruptures can occur decades after fabrication. As a consequence of the resulting insecurity with respect to the useful life of prestressed concrete structures, it has been found to be important to be able to detect ruptures of individual wires promptly.

BACKGROUND OF THE INVENTION

The nondestructive testing of the integrity of steel reinforcements of prestressed concrete structures by magnetic field detection is known in which ruptures in structural members with a direct bond between the concrete and the reinforcement (i.e. with reinforcement wires which are not surrounded by a metallic sheathing type) can be detected by a nondestructive process (magnetic stray field measurement). For structures with an additional bond in which the sheathing effect of the sheathing tube and the neighboring intact steel reinforcement must be considered, a process has been proposed in which the incorporated steel reinforcement is subjected to magnetization initially, for example by the effect of permanent magnets moved along the surface of the prestressed concrete structure and demagnetization follows of the slack reinforcement (DE-OS 40 37 992 and 40 37 993).

SUMMARY OF THE INVENTION

According to the invention the integrity monitoring of the stressing elements of prestressed concrete structures is facilitated and improved substantially by magnetization of the stressing elements before their incorporation since, in this manner, one need not fear any restriction in the magnetization by poorly accessible regions at which reinforcing elements are particularly important.

The prior magnetization of the reinforcement member is apparently advantageous, independently of the nature of its use, in both direct bonding or with a sheathing tube. In the latter case, especially depending upon the sheathing material, a magnetization of the core can be effected together with the sheathing tube. Preferably, however, the magnetization of the reinforcing steel is effected prior to drawing it into the sheathing tube.

The subsequent monitoring of the reinforcing steel within the prestressed concrete structure or installation in the sense of detecting individual breaks is effected also with the premagnetized steel used in the invention in a known manner by repetitive magnetic field sensing. The prior magnetization in the longitudinal direction can be achieved simply in that the reinforcement steel is passed through a coil supplied with direct current. The inspection is effected by measuring the magnetic field at the surface of the structure. Breaks within the reinforcement bundle are detectable as anomalies in the external field and can thus be localized by magnetic field sensors. Depending upon the signal strength, which is dependent, for example, upon the position of the reinforcing steel, different magnetic field sensors (listed in accordance with increasing sensitivity, e.g. Hall-effect sensors, Förster sensors, stationary SQUIDs with pick-up coils, traveling SQUID) can be used. The magnetic field sensor is displaced on the structure surface with the aid of a suitable displacement and positioning device and the signals are picked up with data processing.

If there is a broken reinforcing steel in a bundle, i.e. it is surrounded by other reinforcing steels and a sheathing tube, the rupture location is indicated by a local maximum.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
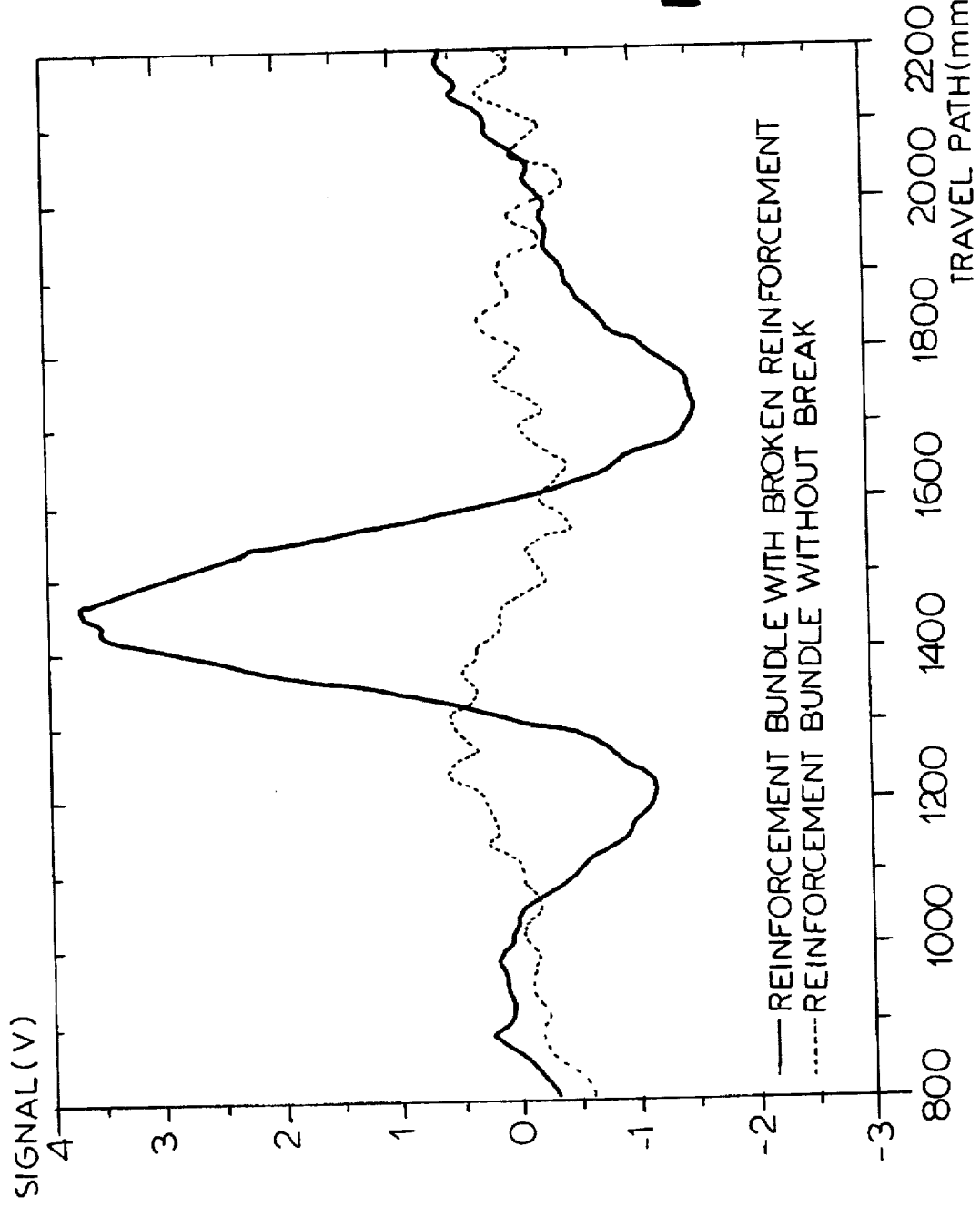
FIG. 1 is a graph plotting the travel path in mm along the surface of a structure provided with a reinforcing steel bundle vs. The signal obtained by measurement with a displaceable pick up coil and a SQUID.

In FIG. 1 a measurement on a reinforcing steel bundle with an outer diameter of 75 mm and 40 reinforcing members is shown. In the first case there is no break in the central reinforcing member and in the second case a broken and premagnetized reinforcing member with a spacing of the break surfaces of 0.2 mm is represented.

The measurement was carried out with a stationary SQUID and a displaceable pick-up coil (spacing of pick-up coil-reinforcement steel bundle=300 mm).

By contrast, in a conventional measuring process to detect steel reinforcement breaks, an outer magnetic field applied by means of a yoke or a permanent magnet so that the magnetization effect is shielded and the stray field at the break location can no longer be detected. With unbroken steel reinforcement, no field anomalies are detected (zero measurement). Since during the inspection there is no impingement of a magnetic field on the girder, additional ferromagnetic elements, e.g. stirrups are not magnetized and thus do not produce any further magnetic field signals. From this it can be concluded that usually there is no significant decay of the magnetization of the incorporated reinforcing steel with time (especially as can be locally differentiated). The strength and mechanical characteristics of the steel reinforcement are not altered by the magnetization. One cannot expect any effect from surrounding components in the structure either.

Figure 2:
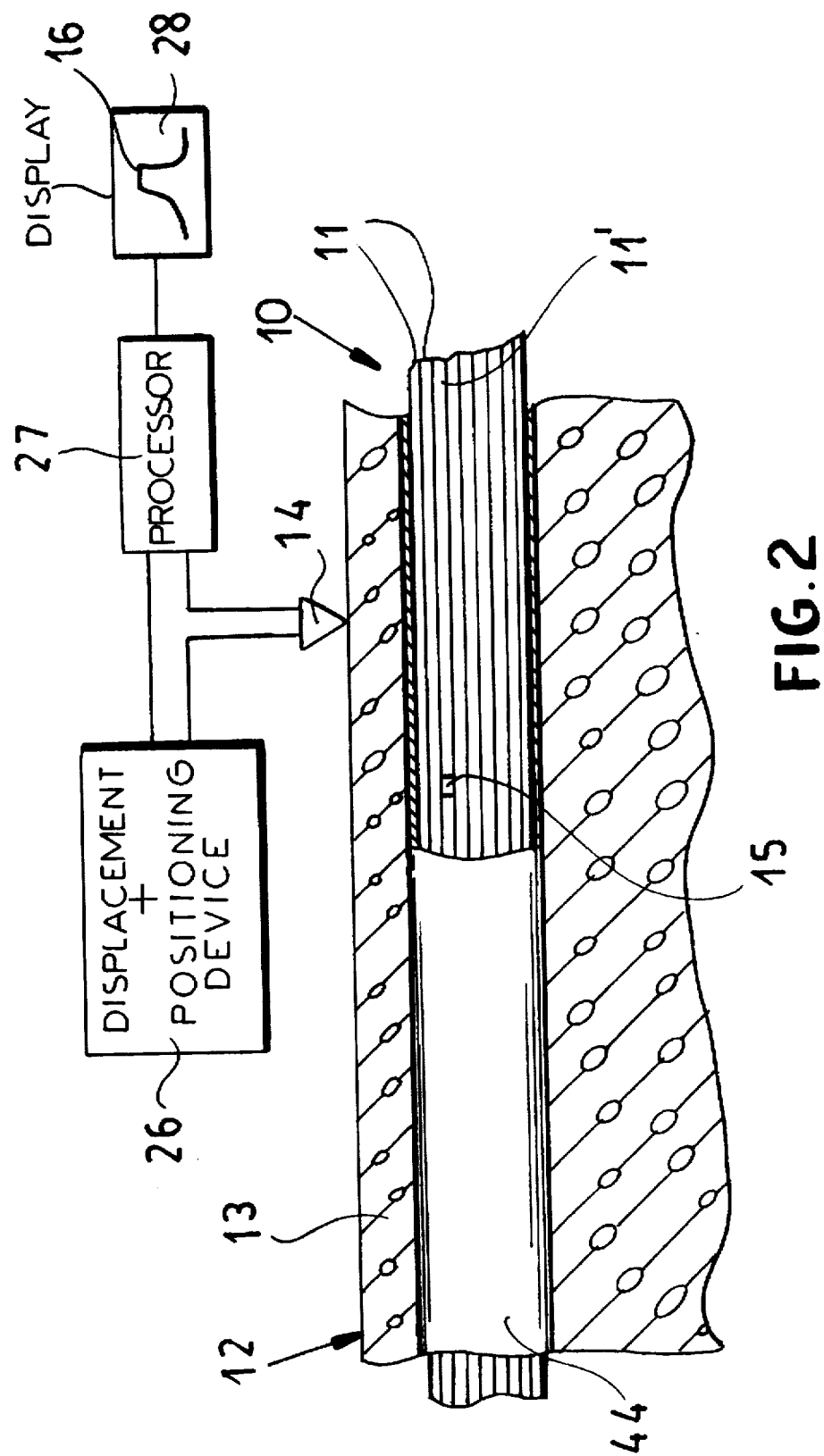
FIG. 2 is a diagrammatic cross sectional view illustrating the detection of a break in a premagnetized reinforcing member.
Figure 3:
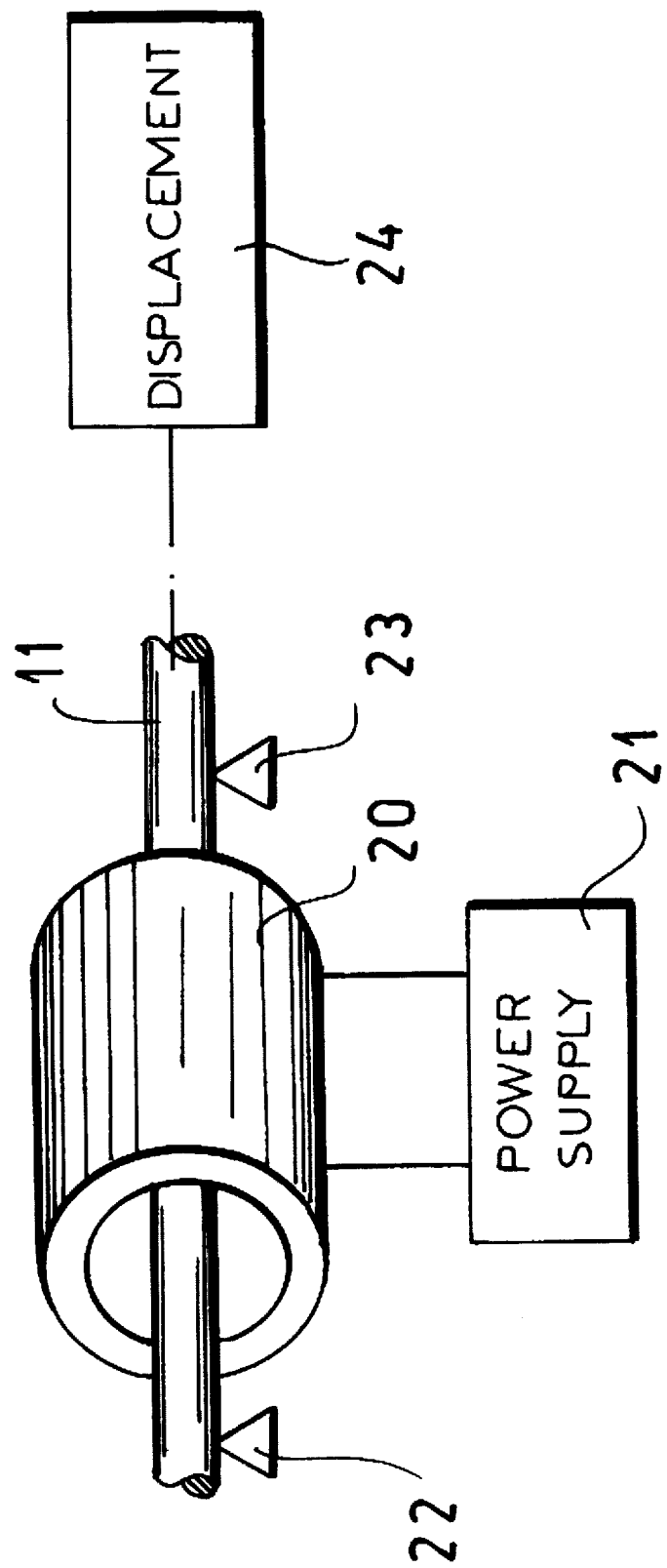
FIG. 3 is a diagram illustrating the magnetization of a reinforcing member.

As can be seen from FIG. 2, the bundle 10 of reinforcing members 11 can be embedded in the structure 12, along the surface 13 of which the sensor 14 is displaceable. A sheath as previously described is shown at 44 around the bundle. The reinforcing members are premagnetized by drawing each of them as shown in FIG. 3 through a coil 20 supplied with direct current from the power supply 21, the magnetizing apparatus including holding or guide elements 22 and 23 for passing the reinforcing element through the coil.

The means for moving the coil relative to the reinforcing element has been represented diagrammatically at 24.

The sensor 14 may be positioned by a displacement and positioning device 26 and is provided with a data processor 27 to form the display 28 which may correspond to the graph of FIG. 1. In FIG. 2 the broken reinforcing member is shown at 11' and has a break at 15, the ends of the ruptured reinforcing element being spaced apart by about 0.2 mm as has previously been described to yield the peak 16 in the display (compare FIG. 1).

We claim:

1. A method of producing and verifying integrity of a structure, comprising the steps of:

(a) at a construction site, magnetizing each of a plurality of elongated ferromagnetic reinforcing members externally of said structure to impart thereto a magnetic field strength detectable at a surface of said structure;

(b) embedding said reinforcing members as magnetized in step (a) under tension in a material shaped to form said structure so that said reinforcing members extend in said structure along a surface of said structure; and (c) for subsequent evaluation of integrity of said structure, displacing a magnetic field sensor along said surface and, without magnetization of said members during measurement, measuring a remanent magnetic field from the previously magnetized reinforcing members solely resulting from the magnetization in step (a) and recording a measurement of the magnetic field as a function of displacement of said sensor along said surface, thereby detecting a break in said members.

2. The method defined in claim 1 wherein said ferromagnetic reinforcing members are magnetized at said construction site by passing said elongated ferromagnetic reinforcing members through a coil energized by direct current.

3. The method defined in claim 1 further comprising the step of surrounding said reinforcing members with a tubular sheath.

4. The method defined in claim 1 wherein said structure is a concrete structure and said reinforcing members are composed of steel.

5. A reinforced concrete structure comprising a body of concrete and a plurality of elongated premagnetized ferromagnetic reinforcing members embedded in said body and having a magnetic field strength imparted thereto externally of said body sufficient for detection of said magnetic field strength at a surface of said structure without additional magnetism of said members.

\* \* \* \* \*